(12) United States Patent
Yan

(10) Patent No.: US 7,396,524 B2
(45) Date of Patent: Jul. 8, 2008

(54) METHODS FOR SCREENING COMPOUNDS FOR PROARRHYTHMIC RISK AND ANTIARRHYTHMIC EFFICACY

(75) Inventor: Gan-Xin Yan, Villanova, PA (US)

(73) Assignee: Main Line Health Heart Center, Wynnewood, PA (US)

( * ) Notice: Subject to any disclaimer, the term of this patent is extended or adjusted under 35 U.S.C. 154(b) by 327 days.

(21) Appl. No.: 11/194,983

(22) Filed: Aug. 2, 2005

(65) Prior Publication Data

US 2007/0031817 A1 Feb. 8, 2007

(51) Int. Cl.
A61K 49/00 (2006.01)
(52) U.S. Cl. ...................................................... 424/9.2
(58) Field of Classification Search ........................ None
See application file for complete search history.

(56) References Cited

U.S. PATENT DOCUMENTS

| 6,847,840 B2 | 1/2005 | DePasquale et al. | 600/516 |
| 2003/0013136 A1 | 1/2003 | Balser et al. | 435/7.21 |
| 2003/0108924 A1 | 6/2003 | George et al. | 435/6 |
| 2003/0235838 A1 | 12/2003 | Keating et al. | 435/6 |
| 2004/0161805 A1 | 8/2004 | Heylen et al. | 435/7.2 |
| 2004/0170993 A1 | 9/2004 | Fishman et al. | 435/6 |

OTHER PUBLICATIONS

Takahara et al. AJH May 2003 vol. 16(5):part 2, (abstract).*
Thomas et al. J of Cardiovascular Pharmacology 2003 41:140-147.*
Owens et al. Pharmacotherapy 2002 22(5):663-672.*
Antzelevitch, C. et al., "Cellular and ionic mechanisms underlying erythromycin-induced long QT and torsade de pointes," *J. Am. Coll. Cardiol.* 1996; 28(7):1836-1848.
Antzelevitch, C. et al., *J Cardiovasc Electrophysiol* 2003; 14:114-115.
Banyasz, T. et al., "Endocardial versus epicardial differences in L-type calcium current in canine ventricular myocytes studied by action potential voltage clamp," *Cardiovasc Res* 2003; 58: 66-75.
Bosse E., et al., "Stable and functional expression of the calcium channel α1 subunit from smooth muscle in somatic cell lines," *EMBO J.* 1992; 11:2033-2038.
Champeroux, P. et al., "Prediction of the risk of Torsade de Pointes using the model of isolated canine Purkinje fibres," *Br.J. Pharmacol.* Feb. 2005;144:376-385.
Clancy & Rudy., "Linking a genetic defect to its cellular phenotype in a cardiac arrhythmia," *Nature* 1999; 400: 566-569.
Coumel, P. et al., "Evaluation of drug-induced QT interval modifications in dynamic electrocardiography: the case of bepridil," *Fundam. Clin. Pharmacol.* 1993; 7: 61-68.
Coumel P. et al., "Safety of Bepridil: From Review of the European Data," *Am. J Cardiol* 1992; 69:75D-78D.
Doerr, T. et al., "Ionic currents contributing to the action potential in single ventricular myocytes of the guinea pig studied with action potential clamp," *Pflugers Arch* 1990; 416: 230-237.
Franz, M. R., "Current status of monophasic action potential recording: theories, measurements and interpretations," *Cardiovasc. Res.* 1999; 41:25-40.
Gerhardy, A. et al., "Generating and influencing Torsades de Pointes—like polymorphic ventricular tachycardia in isolated guinea pig hearts," *Basic Res. Cardiol.* 1998; 93: 285-294.
Gintant, G. A. et al., "The Canine Purkinje Fiber: An In Vitro Model System for Acquired Long QT Syndrome and Drug-Induced Arrhythmogenesis," *J Cardiovasc Pharmacol* 2001; 37:607-618.
Han, W. et al., "Ionic Remodeling of Cardiac Purkinje Cells by Congestive Heart Failure," *Circulation*, 2001; 2095-2100.
Hondeghem, L. M., et al., "Instability and Triangulation of the Action Potential Predict Serious Proarrhythmia, but Action Potential Duration Prolongation Is Antiarrhythmic," *Circulation*, 2001;103:2004-13.
Joshi, A. et al., "Preclinical Strategies to Assess QT Liability and Torsadogenic Potential of New Drugs: The role of Experimental Models," *J Electrocardiol*, 2004; 37 Suppl: 7-14.
Kang M-G. et al., "γ Subunit of Voltage-activated Calcium Channels," *J. Biol. Chem.* 2001; 279:32917-32924.
Krichhof, P. et al., "Amiodarone-Induced Postrepolarization Refractoriness Suppresses Induction of Ventricular Fibrillation," *J Pharmacol Exp Ther* 2003; 305: 257-263.
Kowey and Yan, "Proarrhythmias and Antiarrhythmias: Two Sides of the Same Coin," *Heart Rhythm*, Sep. 2005, 2(9): 957-959.
Lacinova, L. et al., "The block of expressed L-type calcium channel is modulated by the $\beta_3$ subunit," *FEBS Lett.* 1995; 737:103-7.

(Continued)

*Primary Examiner*—Jon P Weber
*Assistant Examiner*—Bin Shen
(74) *Attorney, Agent, or Firm*—Ratner Prestia

(57) ABSTRACT

Methods for screening compounds for their potential to induce or inhibit a cardiac arrhythmia are disclosed. The methods comprise determining the ratio of the time constant ($\tau$) of $I_{Ca,L}$ recovery in tissue expressing the L-type calcium channel or any subunit or combination thereof of the L-type calcium channel treated with a test compound to the ventricular repolarization time of cardiac tissue treated with a test compound. The methods further comprise determining an arrhythmic risk score for a specified dose of a test compound.

20 Claims, 9 Drawing Sheets

OTHER PUBLICATIONS

Linz and Meyer, "Profile and kinetics of L-type calcium current during the cardiac ventricular action potential compared in guinea-pigs, rats and rabbits," *Pflugers Arch.* 2000; 439:588-599.

Lu, H. R. et al., "Species Plays an Important Role in Drug-Induced Prolongation of Action Potential Duration and Early Afterdepolarizations in Isolated Purkinje Fibers," *J Cardiovasc Electrophysicol*, 2001; 12: 93-102.

Mattioni, T. A. et al., "Aminodarone in Patients with Previous Drug-Mediated Torsade de Pointes," *Ann. Intern. Med.* 1989;111:574-580.

Owens, R. C., Jr., "QT Prolongation with Antimicrobial Agents—Understanding the Significance," *Drugs*, 2004; 64: 1091-1124.

Peng, S. et al., "Effects of Methylmercury on Human Neuronal L-Type Calcium Channels Transiently Expressed in Human Embryonic Kidney Cells (HEK-293)," *J. Pharmacol. Exp. Ther.* 2002; 302:424-432.

Rampe, D. et al., "A mechanism for the proarrhythmic effects of cisapride (Propulsid): high affinity blockade of the human cardiac potassium channel HERG," *FEBS Lett*, 1997; 417:28-32.

Rials, S. J. et al., "Regression of Left Ventricular Hypertrophy With Captopril Restores Normal Ventricular Action Potential Duration, Dispersion of Refractoriness, and Vulnerability to Inducible Ventricular Fibrillation," *Circulation* 1997; 96:1330-1336.

Roden, D. M. "Drug-Induced Prolongation of the QT Interval," *N Engl. J. Med.* 2004; 350:1013.

Sanguinetti, M. C., et al., "A Mechanistic Link between an Inherited and an Acquired Cardiac Arrhythmia: HERG Encodes the $I_{Kr}$ Potassium Channel," *Cell* 81:299-307 (1995).

Seisenberger, C., et al., "Two stable cell lines for screening of calcium channel blockers," *Naunyn Schmiedebergs Arch. Pharmacol.* 1995; 352:662-669.

Studenik, C. R. et al., "Differences in action potential and early afterdepolarization properties in LQT2 and LQT3 models of long QT syndrome," *Br J Pharmacol* 2001; 135:85-92.

Traebert, M. et al., "Inhibition of hERG $K^+$ currents by antimalarial drugs in stably transfected HEK293 cells," *Eur. J. Pharmacol.* 2004; 484:41-48.

van Opstal, J. M. et al., "Chronic Amiodarone Evokes No Torsade de Pointes Arrhythmias Despite QT Lengthening in an Animal Model of Acquired Long-QT Syndrome," *Circulation* 2001; 104:2722-2727.

Viswanathan & Rudy., "Pause induced afterdepolarizations in a long QT syndrome: a simulation study," *Cardiovasc Res.* 1999; 42: 530-542.

Welling, A., et al., "Stable Co-Expression of Calcium Channel $\alpha_1$, $\beta$ and $\alpha_2/\delta$ Subunits in a Somatic Cell Line," *J. Physiol.* 1993; 471:749-765.

Yan, G.-X. et al., "Characterisitcs and Distribution of M Cells in Arterially Perfused Canine Left Ventricular Wedge Preparations," *Circulation* 1998; 98: 1921-1927.

Yan, G.-X. et al., "Ventricular hypertrophy amplifies transmural repolarization dispersion and induces early afterdepolarization," *Am. J. Physiol.* 2001 281: H1968-H1975.

Yan, G.-X. et al., "Phase 2 Early Afterdepolarization as a Trigger of Polymorphic Ventricular Tachycardia in Acquired Long-QT Syndrome," *Circulation* 2001; 103:2851-2856.

Yan, G.-X. et al., "Ventricular Repolarization Components on the Electrocardiogram," *J Am Coll Cardiol* 2003; 42: 401-409.

Yang, T. et al., "Drug Block of $I_{Kr}$: Model Systems and Relevance to Human Arrhythmias," *J. Cardiovasc. Pharmacol.* 2001; 38: 737-744.

Yang, T. et al., "Extracellular Potassium Modulation of Drug Block of $I_{Kr}$. Implications for Torsade de Pointes and Reverse Use-Dependence," *Circulation* 1996; 93: 407-411.

Yasuda T., et al., "Overexpressed $Ca_v\gamma3$ Inhibits N-type ($Ca_v2.2$) Calcium Channel Currents through a Hyperpolarizing Shift of "Ultra-slow" and "Closed-state" Inactivation," *J. Gen. Physiol.* 2004; 123:401-416.

Zygmunt, A. C. et al., "$I_{to1}$ dictates behavior of $I_{Cl(Ca)}$ during early repolarization of canine ventricle," *Am J Physiol*, 1997; 273: H1096-H1106.

Chaiang, C.-E., et al., "Effects of sildenafil on cardiac repolarization," Cardiovascular Res., 2002, 55, 290-299.

Hirano, Y., et al., "$Ca^{2+}$ entry-dependent inactivation of L-type Ca current: a novel formulation for cardiac action potential models," Biophysical J., 2003, 84, 696-708.

Linz, K. W., et al., "Control of L-type calcium current during the action potential of guinea-pig ventricular myocytes," J. of Physiology, 1998,513(2), 425-442.

Shryock, J.C., et al., "A mechanistic approach to assess the proarrhythmic risk of QT-prolonging drugs in preclinical pharmacologic studies," J. Electrocardiology, 2004, 37(Suppl.), 34-39.

* cited by examiner

METHODS FOR SCREENING COMPOUNDS FOR PROARRHYTHMIC RISK AND ANTIARRHYTHMIC EFFICACY

FIELD OF THE INVENTION

The present invention relates generally to the field of safety pharmacology. In particular, the invention features novel methods for screening compounds for their potential to induce a cardiac arrhythmia or to inhibit a cardiac arrhythmia in a subject, as well as methods to generate a risk score for distinguishing among different compounds' capacity to cause torsade de pointes.

BACKGROUND OF THE INVENTION

Various publications, including patents, published applications, technical articles and scholarly articles are cited throughout the specification. Each of these cited publications is incorporated by reference herein, in its entirety, for all that it teaches.

Ventricular repolarization time is determined by transmembrane action potential duration (APD) of the ventricular myocardium or the QT interval on the body surface electrocardiogram (ECG). Delayed ventricular repolarization that manifests as QT interval prolongation on the ECG is associated with the development of an atypical form of polymorphic ventricular tachycardia termed torsade de pointes (TdP) that can result in recurrent fainting and sudden death in humans. An increasing number of medications are found to prolong ventricular repolarization, leading to QT prolongation. Some of these medicines are developed purposefully to prolong cardiac APD for the treatment of cardiac arrhythmias such as atrial fibrillation and monomorphic ventricular tachycardia. These medications are called antiarrhythmic drugs, and include sotalol, dofetilide and amiodarone. Many such drugs are administered in suboptimal doses to avoid TdP. However, suboptimal dosing of these drugs in humans in order to avoid TdP greatly attenuates their efficacy in the inhibition of cardiac arrhythmias. On the other hand, many non-cardiac agents, such as cisapride, terfenadine, erythromycin and sparfloxacin, have been removed from the market or relabeled for restricted use because of their proarrhythmic potential. Recent regulatory guidelines recommend preclinical assessment of potential new drugs for QT prolongation and the resultant risk of TdP in humans.

Several technologies and methods are currently available for preclinical testing of compounds for their potential to cause TdP. One such method is to measure a drug's effect on the ionic current in stable cell lines that express the hERG channel. In humans, the ether-a-gogo related gene (hERG) potassium ($K^+$) channels play a role in the control of action potential duration in cardiac cells. In the cell, this $K^+$ channel underlies the cardiac repolarizing $K^+$ current $I_{kr}$, returning the cell to its resting state. (Sanguinetti, M. C., et al. *Cell* 81:299-307 (1995)). Because blockage of the hERG channel generally results in prolongation of the action potential, as well as the prolongation of the QT interval, the effect of a drug on the $I_{kr}$ current is thought to be correlated with the drug's potential to cause TdP. (Joshi A K et al., *J. Electrocardiol.* 2004; 34(supplement): 7-14).

This screening method, however, suffers from several major drawbacks. The drawbacks include the fact that this method is not well suited for high throughput screening, and that TdP risk is not proportional to the potency of a compound to inhibit hERG current. In other words, this method has a fairly high potential to produce false negatives and positives. A false negative may result if the hERG channel is not the $K^+$ channel target of the compound. False positives may result where the blockage of the hERG channel does not directly correlate with a prolonged QT interval. In addition to the $I_{kr}$ current, there are other ventricular membrane currents which may be affected by a drug. The ventricular action potential duration, which determines the QT interval, is the consequence of a dynamic balance of multiple membrane currents. Thus, testing only the effect of a drug on the $I_{kr}$ current, may overlook the drug's effect on other membrane currents such as those produced by Calcium or Sodium ion channels, thereby blurring the picture of the drug's effect on the QT interval. The typical examples are verapamil and amiodarone. Verapamil is a potent hERG current inhibitor, yet is not associated with significant QT prolongation and is free of TdP risk in humans (Yang T et al., *J. Cardiovasc. Pharmacol.* 2001; 38: 737-744). Similarly, amiodarone inhibits hERG current at fairly low concentrations and significantly prolongs the QT interval, although it rarely causes TdP in humans (Mattioni T A et al. *Ann. Intern. Med.* 1989; 111: 574-580).

A second screening method involves the direct measurement of action potential duration in isolated ventricular Purkinje fibers or ventricular myocardium. The rationale behind this method is the expectation that a compound would be likely to cause TdP if it can be shown to increase action potential duration. (Champeroux, P., et al. *Br. J. Pharmacol.* 144:376-85 (2005)). This screening method, however, is not a very sensitive assay, and thus is generally done in conjunction with another screen such as hERG inhibition.

This screening method also suffers from an additional drawback in that it has a high potential to cause false positive or negative results. Examples of false positives include drugs such as amiodarone, which may cause a prolonged action potential duration or QT interval (van Opstal J M et al., *Circulation* 2001; 104:2722-2727), yet not be potent inducers of TdP. Examples of false negatives include the drugs bepridil and terfenadine, which are known to cause TdP in humans, but have not been shown to produce a significant increase in the action potential duration of the Purkinje fiber (Champeroux et al., *Br. J Pharmacol.* 2005; 144:376-385). Experimental data show that bepridil fails to produce a significant increase in the QT interval (Coumel et al., *Fundam. Clin. Pharmacol.* 1993; 7: 61-68), although it is associated with a significant risk of TdP and sudden death (Coumel P et al., *Am. J. Cardiol* 1992; 69: 75D-78D). Thus, the lack of sensitivity of this assay may result in a compound's true propensity to cause TdP to go unrecognized in preclinical screening.

A third screening method involves the measurement of the QT interval or the duration of monphasic action potential in the isolated, Langendoff-perfused heart. (Hondeghem, L. M., et al., *Circulation,* 2001; 103:2004-13). This method suffers from a significant drawback as well. The drawback is that the electrical stability of the perfused heart preparations is of relatively short duration, on the magnitude of less than two hours. The instability of the preparations may thus result in false negative or false positive results.

Interestingly, the QT interval (or ventricular APD) seems to be positively proportional to body mass among various species under physiological conditions, ranging from tens of milliseconds in mice to hundreds of milliseconds in large animals as shown in FIG. 1. APD prolongation in small animals to an extent may lead to occurrence of early after depolarization (EAD) capable of initiating TdP, but in larger species, the same or longer APDs can be physiological. For example, the physiological QT interval in the cow is approximately 400 ms, but the same length of QT would be likely associated with a high risk of TdP in the rabbit. This raises a compelling question: what is the mechanism that dictates if a prolonged QT interval is physiological or pathophysiological? Apparently, there is a mechanism for stabilizing cell membrane potentials in the large species, so that a normal heart rhythm can be maintained under a relatively longer QT interval.

TdP is triggered by ventricular action potential EAD at repolarization phase 2 or phase 3. In other words, EAD as the trigger plays a central role in the development of TdP, and its occurrence in ventricular action potentials could serve as a marker to determine if a prolonged QT interval is physiological or pathophysiological. Since the L-type calcium channel current ($I_{Ca}$) is the primary charge carrier for phase 2 EADs under delayed ventricular repolarization (Clancy & Rudy., *Nature* 1999; 400: 566-569; Viswanathan & Rudy., *Cardiovasc Res.* 1999; 42: 530-542), its availability after the initial activation for the development of EAD during repolarization phase 2 is critical for the development of TdP.

The foregoing discussion indicates that there exists a need for an economical and more accurate procedure to screen compounds for their capacity to cause a prolonged QT interval and potentially life-threatening cardiac arrhythmias such as TdP. Similarly, there exists a need for an economical and more accurate procedure to screen compounds for their anti-arrhythmic potential. Such accurate procedures would have substantial implications for the pharmaceutical industry's development of drugs to treat cardiac arrhythmias without the adverse side effect of causing an arrhythmia or other adverse condition, as well as for the development of non-cardiac therapeutic agents. It is desirable that such a method significantly reduce, and even more preferably eliminate, false positive and false negative results. It is also desirable that such a method be amenable to high throughput screening. The present invention is directed to a more accurate procedure, and addresses these long-felt needs.

SUMMARY OF THE INVENTION

The present invention features methods to screen compounds for their potential to induce or inhibit a cardiac arrhythmia. In one aspect of the invention, the methods comprise determining the ratio of the time constant ($\tau$) of $I_{Ca,L}$ recovery in tissue expressing the L-type calcium channel or any subunit or combination thereof of the L-type calcium channel treated with a test compound to the ventricular repolarization time of cardiac tissue treated with a test compound. In a detailed aspect, the ratio is determined by measuring the ventricular repolarization time of cardiac tissue treated with a test compound, measuring the recovery of the L-type calcium channel current ($I_{Ca,L}$) in tissue expressing the L-type calcium channel or any subunit of the L-type calcium channel, calculating the time constant ($\tau$) of $I_{Ca,L}$ recovery in the tissue expressing the L-type calcium channel or any subunit of the L-type calcium channel, and calculating the ratio of the time constant ($\tau$) of $I_{Ca,L}$ recovery to the ventricular repolarization time.

In a further detailed aspect, the ventricular repolarization time is measured by a glass microelectrode or monophasic action potential electrode or an electrocradiogram or is measured by an electrogram using unipolar or bipolar electrodes, and the L-type calcium channel recovery is measured by a voltage clamp such as a whole-cell voltage clamp, which can employ a double pulse protocol. The L-type calcium channel recovery can be measured on any cardiac tissue, or any tissue expressing the L-type calcium channel or any subunit or combination of subunits of the L-type calcium channel, such as stable cell lines. The test compound is assessed for its effect on the ventricular repolarization time and recovery of the L-type calcium channel current at multiple doses, which span a range from the compound's free therapeutic plasma $C_{max}$ to a concentration equal to or greater than 500-fold over the $C_{max}$.

In another aspect, the methods of the present invention feature determining a TdP risk score by comparing the ratio of the time constant ($\tau$) of $I_{Ca,L}$ recovery to the ventricular repolarization time for the test compound to the ratio of the time constant ($\tau$) of $I_{Ca,L}$ recovery to the ventricular repolarization time of a standard having an established risk.

DETAILED DESCRIPTION OF ILLUSTRATIVE EMBODIMENTS

Figure 1A:
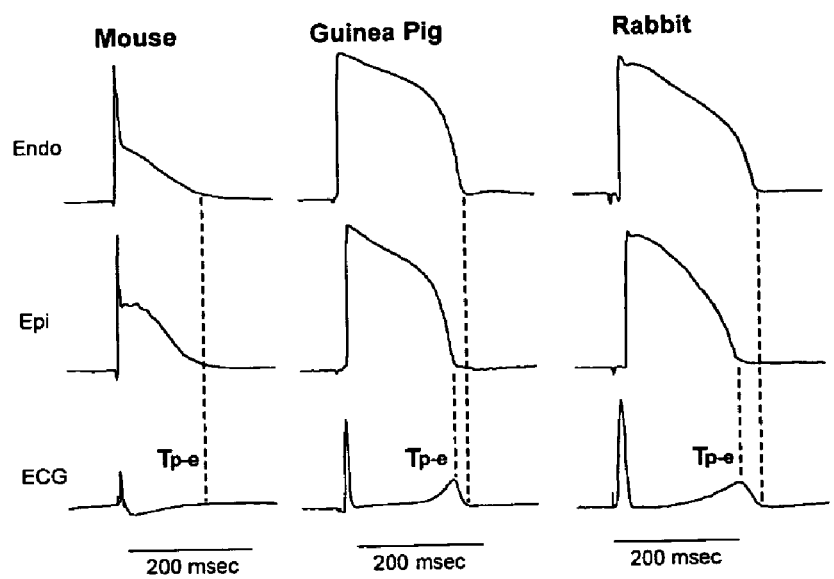
FIG. 1. Proportion of QT Interval to Body Mass. (a). Original recordings of transmembrane action potentials from endocardium (Endo) and epicardium (Epi) and ECG from the mouse, guinea pig, and rabbit left ventricular wedge preparations. (b). Original recordings of transmembrane action potentials from subendocardium (Subendo) and Epi and ECG from the canine and cow left ventricular wedge preparations. $T_{p-e}$ represents the interval from the peak to the end of T wave. (c). Graphical depiction of the relationship between the action potential duration and left ventricular wall thickness. (d). Graphical depiction of the relationship between transmural dispersion of repolarization and left ventricular wall thickness.
Figure 1B:
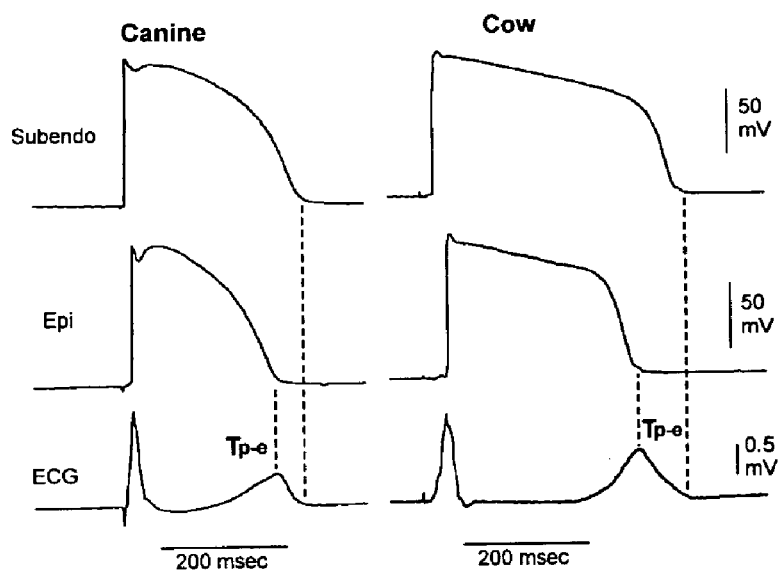
Figure 1C:
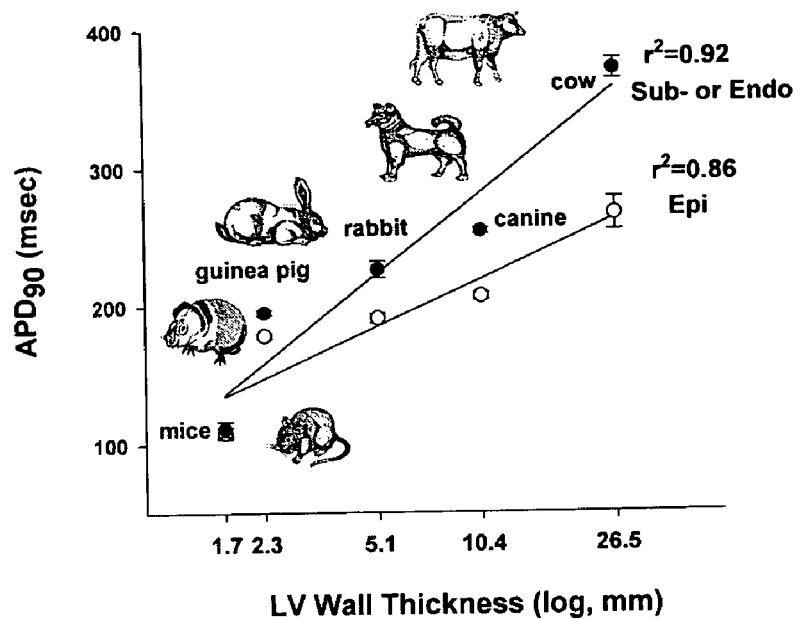
Figure 1D:
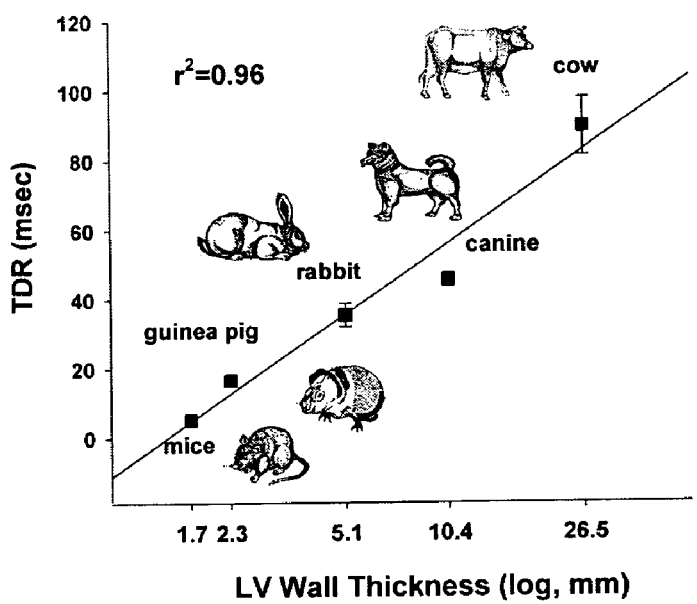

Definitions:

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

As used herein, the term "proarrhythmic" refers to any tendency to induce any variation in the normal physiology or rhythm of a heartbeat in a subject, including without limitation tachycardia, bradycardia, and fibrillation.

As used herein, the term "antiarrhythmic" refers to any tendency to correct, restore, or otherwise remedy any variation in the normal physiology or rhythm of a heartbeat in a subject.

"Repolarization" refers to the reestablishment of polarity, especially the return of cell membrane potential to resting potential after depolarization, in excitable tissue such as cardiac tissue.

"Excitable tissue" refers to any tissue that can generate an electrical impulse or can be activated by an electrical stimulus. Such tissue include without limitation skeletal muscle, smooth muscle, cardiac tissue, and nervous tissue.

"Action potential duration" as used herein with respect to the ventricles of the heart refers to the time between the start of depolarization and the end of repolarization of myocytes in the ventricles and ventricle tissue of the heart. In cardiac tissue, action potential duration can be measured using microelectrodes, and the longest action potential duration of ventricles manifests as the QT interval on the electrocardiogram.

"Long QT" or "LQT" refers to any prolongation of the normal time between the start of depolarization and the end of repolarization of the ventricles and ventricle tissue of the heart, which is manifest on the QT interval of an electrocardiogram.

As used herein, "measure" or "determine" refers to any qualitative or quantitative determinations.

"Recovery" refers to the availability of L-type $Ca^{2+}$ channel for reactivation after inactivation.

As used herein, "tissue" refers to any cell or group of cells. "Cardiac tissue" refers specifically to any cell or group of cells isolated by any means from the heart of an animal.

"Stable cell" or "stable cell line" refers to any cell in which any subunit of the L-type calcium channel or combinations thereof, including the whole L-type calcium channel, can be expressed so that the kinetics of $I_{Ca,L}$ recovery can be examined.

Description:

Drug-induced cardiac proarrhythmia and antiarrhythmia are two sides of the same coin. Efficacy of some antiarrhythmic drugs, e.g., sotalol, dofetilide and amiodarone, to inhibit cardiac arrhythmias, including atrial fibrillation and monomorphic ventricular tachycardia, is expected to reflect their effect to prolong cardiac action potential duration, i.e., cardiac repolarization time. However, an excessively prolonged ventricular repolarization time, which manifests as QT interval prolongation on the body surface ECG, is associated with atypical form of polymorphic ventricular tachycardia termed TdP, resulting in recurrent syncope and sudden death in humans. On the other hand, an increasing number of non-cardiac drugs have been found to prolong QT and cause TdP. These drugs were removed from the market or relabeled for restricted use (Roden, *N Engl. J. Med.* 2004; 350:1013). This has resulted in more vigorous review for new drugs by regulatory agencies to determine such drugs' capacity to cause TdP in humans.

Since TdP occurs often under conditions of QT prolongation, the QT interval or APD and the inhibition of related ionic currents such as hERG current have been considered as a surrogate of TdP. Clinical data indicate that the risk of TdP is not proportional to QT prolongation. A QT interval can be physiological in one species but pathophysiogical in another. For example, the physiological QT interval in the cow is approximately 400 ms, but the same length of QT would be likely associated with a high risk of TdP in the rabbit. Therefore, it stands to reason that there is a mechanism for stabilizing cell membrane potentials in the large species, such that a normal heart rhythm can be maintained under a relatively longer QT interval. The present invention is derived from the data that indicate an intrinsic balance between $I_{Ca,L}$ recovery and ventricular myocyte repolarization under physiological conditions in various species. The impairment of this intrinsic balance by drugs either by prolongation of repolarization time or by acceleration of $I_{Ca,L}$ recovery can result in fluctuation of cell membrane potentials during repolarization phase 2 (i.e., phase 2 EAD) that is capable of initiating TdP. Therefore, the present invention provides novel methods to screen test compounds for their effect on this intrinsic balance. The methods can be practiced according to the details below.

Test Compounds:

The present invention can be applied in a range of applications. One application of particular value to researchers and drug developers is to test an existing or candidate pharmaceutical compound for its effect on ventricular repolarization and $I_{Ca,L}$ recovery. Thus, the methods of the present invention can assist in the identification of compounds that are likely to give rise to a cardiac arrhythmia. This knowledge can identify and/or minimize the risk to a patient taking such pharmaceuticals that the patient will suffer a cardiac arrhythmia, ventricular defibrillation, or other LQT-related injury. The methods of the present invention are therefore useful for drug design and screening.

The methods of the present invention can be used to screen drug candidates before they are approved for patient use or reach the marketplace. The methods can be used in preclinical or clinical screening. When the methods of the present invention are applied to a candidate pharmaceutical that is in development, a drug designer or researcher can identify a candidate pharmaceutical that is likely to give rise to a proarrhythmic risk and, if desired, subject the compound to appropriate additional testing, or optionally remove the candidate from the research program. This can save a drug developer time and money by identifying those candidate compounds that are not worthy of pursuing in clinical trials. Alternatively, if development is pursued, suitable warning to medical practitioners and patients can be provided, based on data derived from the methods of the present invention. Additionally, since the data derived from the methods of the present invention can be quantitative, the methods offer the ability to gauge the relative LQT effect and TdP risk a given candidate might exhibit.

The methods of the present invention can also be used to screen drugs already approved for patient use and in the marketplace. In this context, the methods can be employed to identify drugs that can pose a risk of TdP and can be marked as such. The methods of the present invention offer benefit not only to those developing drugs, but those to whom these and other drugs are administered. Ultimately, the methods of the present invention offer the ability to prevent the injury or even death of a patient.

"Test compound" or "candidate compound" are used synonymously herein, and refer to any molecule that can be analyzed using the methods of the present invention. Candidate compounds to be tested by the methods of the present invention include purified molecules, substantially purified molecules, molecules that are one or more components of a mixture of compounds, or a mixture of a compound with any other material. Test compounds can be organic or inorganic chemicals, or biomolecules, and all fragments, analogs, homologs, conjugates, and derivatives thereof. Biomolecules include, without limitation, proteins, polypeptides, nucleic acids, lipids, polysaccharides, and all fragments, analogs, homologs, conjugates, and derivatives thereof. Test compounds can be of natural or synthetic origin, and can be isolated or purified from their naturally occurring sources, or can be synthesized de novo. Test compounds can be defined in terms of structure or composition, or can be undefined. The compound can be an isolated product of unknown structure, a mixture of several known products, or an undefined composition comprising one or more compounds. Examples of undefined compositions include cell and tissue extracts, growth medium in which prokaryotic, eukaryotic, and archaebacterial cells have been cultured, fermentation broths, protein expression libraries, and the like.

There are multiple sources of naturally occurring candidate compounds that are readily available to those skilled in the art. Natural compounds can be obtained through libraries of bacterial, fungal, plant, and animal extracts, which are commercially available from a number of sources. Alternatively, the skilled artisan can generate a library of natural compounds according to methods known in the art, for example, by standard extraction and fractionation. The present invention contemplates that any library or natural compound can be modified through standard physical, chemical, biochemical, or molecular biology techniques.

Multiple sources of synthetic candidate compounds are also readily available to those skilled in the art. Numerous methods are available for generating random or directed synthesis, including semi-synthesis, of any number of organic or inorganic chemical compounds. Similarly, libraries of synthetic compounds are commercially available, for example, through Brandon Associates (Merrimake, N.H.) and Aldrich Chemical Co (Milwaukee, Wis.). Alternatively, the skilled artisan can generate a library of synthetic organic or inorganic chemical compounds according to methods known in the art. The present invention contemplates that any library or synthetic compound can be modified through standard physical, chemical, biochemical, or molecular biology techniques.

Cardiac Tissue and Stable Cell Lines:

To practice the methods of the invention, cardiac tissue can be derived from any animal. Preferably, to obtain cardiac tissue, a functional heart is freshly isolated from an animal. The animal from which the heart is isolated can be a mammal such as a mouse, rat, guinea pig, rabbit, cat, dog, monkey, cow, horse, pig, and the like. The heart can be isolated by any methodology acceptable in the art. The whole heart can be used, or certain tissues, or cells, or heart subsections can be isolated from the heart. The isolated cardiac tissue can be isolated from the left or right ventricle of the heart ("cardiac ventricular tissue"), from the left or right atrium of the heart ("cardiac atrial tissue"), or from any other subsection of the heart such as Purkinje fibers. The isolated cardiac tissue can be further reduced to a cell suspension, according to any means suitable in the art.

Stable cells or stable cell lines, in which the entire L-type $Ca^{2+}$ channel or any subunit or combination thereof of the L-type $Ca^{2+}$ channel is expressed, can also be used in the methods of the invention. Stable cells or stable cell lines can be excitable or non-excitable. Such cells or cell lines can be generated de novo, according to any means suitable in the art, or can be those already established in the art. Examples of established stable cells and stable cell lines compatible with the present invention include, but are not limited to human embryonic kidney cells (HEK-293) (Peng, S et al., *J. Pharmacol. Exp. Ther.* 2002; 302:424-432, Traebert M et al., *Eur. J. Pharmacol.* 2004; 484:41-48, Seienberger C, et al., *Naunyn Schmiedebergs Arch. Pharmacol.* 1995; 352:662-669), somatic cells such as Chinese hamster ovary cells (CHO) (Bosse E, et al., *EMBO J.* 1992; 11: 2033-2038, Welling A, et al. *J. Physiol.* 1993; 471:749-765, Lacinova L, et al. *FEBS Lett.* 1995; 737:103-7), *Xenopus* oocytes (Kang M-G et al. *J. Biol. Chem.* 2001; 279:32917-32924, Yasuda T, et al. *J. Gen. Physiol.* 2004; 123:401-416), and the like.

Screening of Test Compounds:

One aspect of the invention features methods to screen compounds to determine the potential of the compounds to induce a cardiac arrhythmia or the potential of the compounds to inhibit a cardiac arrhythmia in a subject, comprising determining the ratio of the time constant ($\tau$) of $I_{Ca,L}$ recovery in tissue expressing the L-type calcium channel or any subunit or combination thereof of the L-type calcium channel treated with a test compound to the ventricular repolarization time of cardiac tissue treated with a test compound. The subject can be any animal such a mammal. Preferably, the subject is a human. The cardiac arrhythmia can be TdP.

In one embodiment, the ratio of the time constant ($\tau$) of $I_{Ca,L}$ recovery in tissue expressing the L-type calcium channel or any subunit or combination thereof of the L-type calcium channel treated with a test compound to the ventricular repolarization time of cardiac tissue treated with a test compound is determined by measuring the ventricular repolarization time of cardiac tissue treated with a test compound, measuring the recovery of the L-type calcium channel current ($I_{Ca,L}$) in tissue expressing the L-type calcium channel treated with the test compound, calculating the time constant ($\tau$) of $I_{Ca,L}$ recovery in tissue expressing the L-type calcium channel, and calculating the ratio of the recovery time constant (τ) of $I_{Ca,L}$ to ventricular repolarization time.

In a preferred embodiment, the effect of the test compound on ventricular repolarization and on the recovery of the L-type calcium channel current in tissue expressing the L-type calcium channel or any subunit or combination thereof of the L-type calcium channel is measured in terms of dose-dependence. When determining the ventricular repolarization time of cardiac tissue treated with a test compound, the cardiac tissue can be treated with a single dose of the test compound, or with multiple doses of the test compound. Similarly, when determining the time constant (τ) of $I_{Ca,L}$ recovery in tissue expressing the L-type calcium channel or any subunit or combination thereof of the L-type calcium channel treated with a test compound, such tissue can be treated with a single dose of the test compound, or with multiple doses of the test compound. In a more preferred embodiment, the test compound is evaluated at multiple dosages ranging from the compound's free maximal therapeutic plasma concentration ($C_{max}$) to a concentration equal to or greater than 1000-fold over the compounds' $C_{max}$. In a still more preferred embodiment, the test compound is evaluated at multiple dosages ranging from the compound's $C_{max}$ to a concentration equal to or greater than 500-fold over the compound's $C_{max}$. In a still more preferred embodiment, the test compound is evaluated at multiple dosages ranging from the compound's $C_{max}$ to a concentration equal to or greater than 250-fold over the compound's $C_{max}$. In a still more preferred embodiment, the test compound is evaluated at multiple dosages ranging from the compound's $C_{max}$ to a concentration equal to or greater than 100-fold over the compound's $C_{max}$. In a still more preferred embodiment, the test compound is evaluated at multiple dosages ranging from the compound's $C_{max}$ to a concentration equal to or greater than 50-fold over the compound's $C_{max}$. In a still more preferred embodiment, the test compound is evaluated at multiple dosages ranging from the compound's $C_{max}$ to a concentration equal to or greater than 30-fold over the compound's $C_{max}$. In still more preferred embodiment, the test compound is evaluated at multiple dosages ranging from the compound's $C_{max}$ to a concentration equal to or greater than 10-fold over the compound's $C_{max}$. $C_{max}$ can be determined according to any means available in the art. The skilled artisan will appreciate that such means are known and routine in the art. The compound can be tested at 1, 2, 3, 4, 5, 6, 7, 8, 9, 10, 11, 12, 13, 14, 15, or more concentrations. The ventricular repolarization is measured at each concentration, and the effect of the test compound is compared against any control suitable in the art, such as Tyrode's solution or other balanced salt solutions without the test compound. Whole blood can also serve as a control.

Ventricular repolarization can be measured on any cardiac tissue. Non-limiting examples of such tissue include freshly isolated ventricular myocytes, freshly isolated Purkinje fibers, freshly isolated ventricular tissue such as the ventricular myocardial layer or papillary muscle, freshly isolated atrial tissue, freshly isolated ventricular or atrial wedge preparations, and the like, as would be appreciated by the skilled artisan. The cardiac tissue can be derived from or isolated by any means acceptable in the art, and from any animal, as exemplified herein. The ventricular action potential can be measured from the endocardium, including papillary muscle, subendocardium (M cells), or Purkinje fibers. Action potential measurement can be carried out using the floating glass microelectrode recording technique in an isolated arterially-perfused ventricular wedge preparation (Yan and Antzelevitch, Circulation 1998; 98: 1921-1927), or standard glass microelectrode recording technique in isolated cardiac tissues (Antzelevitch et al., J. Am. Coll. Cardiol. 1996; 28:1836-1848). Alternatively, monophasic action potential (MAP) can be recorded using MAP recording technique in isolated cardiac tissue or in vivo heart (Franz, Cardiovasc. Res. 1999; 41:25-40). Ventricular repolarization time can also be measured by a body surface ECG, or an electrogram using bipolar or unipolar electrodes. In a preferred embodiment, the temperature of the cardiac tissue preparation is kept in a narrow range close to the physiological temperature of the animal from which the tissue was isolated. Such a range should be within about 0.25, 0.5, 0.75, 1, 1.25, 1.5, 1.75, 2.0, 2.25, 2.5, 2.75, 3, 3.25, 3.5, 3.75, or 4 degrees above or below the physiological temperature. In a more preferred embodiment, the temperature should not exceed 2° C. higher or lower than the physiological temperature of the animal.

In a preferred embodiment, the effect of the test compound on the $I_{Ca,L}$ recovery in cardiac tissue is measured under the same experimental conditions, i.e., same cardiac tissue, animal species, compound doses and dose range, temperature, and the like, as used to measure ventricular repolarization. $I_{Ca,L}$ recovery kinetics is measured before treatment of the cardiac tissue with the test compound, and after treatment of the tissue with the test compound at the same doses used to measure ventricular repolarization. $I_{Ca,L}$ recovery can be measured by any means suitable in the art. Preferably, $I_{Ca,L}$ recovery is measured by action potential voltage clamping techniques. A preferred example of an action potential voltage clamping technique is the whole-cell voltage-clamp technique. This technique has been described by Doerr et al. (Doerr et al., Pflugers Arch 1990; 416: 230-237). In one preferred embodiment, the time course of $I_{Ca,L}$ recovery is examined using a double-pulse protocol. Since the recovery of $I_{Ca,L}$ from inactivation is not only time dependent but also voltage dependent, action potential configuration during phase 1 and 2 may influence $I_{Ca,L}$ recovery. Therefore, the assessment of the kinetics of $I_{Ca,L}$ recovery preferably is performed using the action potential tracing as the first voltage clamp pulse ($P_1$) followed by square pulses ($P_2$). In this embodiment, $P_1$ is initially held at −80 mV and steps to −40 mV to deactivate inward sodium current as well as T-type calcium current. $I_{Ca,L}$ current recovery is then recorded from holding potential of −40 mV. The interpulse intervals ($P_1$-$P_2$) for the voltage clamp range from 5 ms to 600 ms or longer so that $I_{Ca,L}$ reaches its steady state. In this double-pulse protocol, the second pulse is stepped to a potential identical to the overshoot potential of the first clamp pulse. Alternatively, the first voltage clamp pulse can be a square pulse. However, in this case the influence of action potential morphology at phase 2, which can be altered by the test compound, on $I_{Ca,L}$ recovery can not be examined.

In an alternative embodiment, the kinetics of $I_{Ca,L}$ recovery are measured in any tissue or cell line expressing the L-type calcium channel or any subunit or combination of subunits of the channel. Preferably, such tissue or cell line is freshly isolated, and more preferably is isolated from the same animal species in which ventricular repolarization was measured. Examples of tissues that can be used in this embodiment include single ventricular myocytes and single atrial myocytes or stable cells or stable cell lines expressing the entire L-type $Ca^{2+}$ channel or any subunit or combination of subunits of the L-type calcium channel. $I_{Ca,L}$ current recovery kinetics can be measured by voltage clamping as described above.

Following the measurement of the $I_{Ca,L}$ current recovery, the recovery time constant is calculated for each tested compound, including controls, at each dose tested. The peak current ratios of $I_{P2}$ to $I_{P1}$ are plotted on the ordinate as a function of the interpulse interval. The data are then fitted with single exponential ($y=y_0+Ae^{-(x-x0)/\tau}$) to obtain the recovery time constant ($\tau$) of $I_{Ca,L}$. The time constant can be calculated using computer software, such as Microcal Software, Inc., Northampton, Mass.

After calculating the recovery time constant ($\tau$) of $I_{Ca,L}$, the ratio of the recovery time constant ($\tau$) of $I_{Ca,L}$ to ventricular repolarization time is calculated for each test compound, including controls, and at each dose tested. The ratio can be expressed as $\tau$ of $I_{Ca,L}$ divided by the measured ventricular repolarization time that can be action potential duration or the QT interval or the duration of the electrogram.

In a preferred embodiment, the methods of the invention further comprise determining an arrhythmic risk score of a test compound. For example, the present invention contemplates that compounds that have clinically well-established QT prolongation and TdP risk profiles (for example, negative risk, low risk, moderate risk and high risk) can be tested with the inventive methods to determine their ratio of the time constant ($\tau$) of $I_{Ca,L}$ recovery to ventricular repolarization time at various doses and in various animals. Using this information, these drugs can serve as standards against which test compounds can be compared in order to determine and categorize their TdP risk score in a given species at a specified dosage level. Non-limiting examples of drugs that can serve as standards for a negative risk of inducing TdP include loratadine, ciprofloxacin, clomipramine, verapamil, and fluxetine. Non-limiting examples of drugs that can serve as standards for a low risk of inducing TdP include amiodarone, citalopram, flecainide, and moxifloxacin. Non-limiting examples of drugs that can serve as standards for a moderate risk of inducing TdP include bepridil, haloperidol, sparfloxacin, and terfenadine. Non-limiting examples of drugs that can serve as standards for a high risk of inducing TdP include dofetilide, sotalol, quinidine, and cisapride.

The inventive risk score is not intended to be limited to those compounds that have clinically well-established QT prolongation and TdP risk profiles. That is, once a test compound is evaluated according to the methods of the present invention, and the ratio of the recovery time constant ($\tau$) of $I_{Ca,L}$ to ventricular repolarization time is determined for that compound, the compound can serve as a standard against which test compounds can be compared in order to determine and categorize their TdP risk score in a given species at a specified dosage level.

Example 5 and Table 2 below show drugs that have been tested by the methods of the present invention that can serve as non-limiting examples of standards against which test compounds can be compared in order to determine their risk of inducing TdP at a specified dosage level. Thus, a TdP risk score for a specified dose of a test compound can be determined by comparing the ratio of the time constant ($\tau$) of $I_{Ca,L}$ recovery to the ventricular repolarization time for the test compound to the ratio of the time constant ($\tau$) of $I_{Ca,L}$ recovery to the ventricular repolarization time of a standard having an established risk. By way of example, a scoring system to estimate TdP Risk of a test compound based on its effect on ventricular repolarization and the ratio of $I_{Ca,L}$ recovery time constant to endocardial APD$_{90}$ is shown in Table 1 below.

According to the criteria assigned in Table 1, a score of equal to or less than zero indicates no risk of TdP, a score of equal to or less than four, but greater than zero indicates a low risk of TdP, a score of equal to or less than eight, but greater than four indicates a moderate risk of TdP, and a score of eight or greater indicates a high risk of TdP. The criteria, in which the ratio of the recovery time constant ($\tau$) of $I_{Ca,L}$ to ventricular repolarization time is the key element, can be adjusted according to the tissue used to take the measurements.

TABLE 1

A Score System to Estimate TdP Risk* of a Test Compound Based on Its Effect on Ventricular Repolarization and the Ratio of $I_{Ca,L}$ Recovery Time Constant to Endocardial APD$_{90}$

| | Risk Score | | | | | |
|---|---|---|---|---|---|---|
| | −1 | 0 | 1 | 2 | 3 | 4 |
| Percent increase in QT interval or APD | <about −5% | About −5% to <about 10% | About 10% to <about 20% | About 20% to about 30% | About 30%- about 50% | >50% |

| | Risk Score | | | | | |
|---|---|---|---|---|---|---|
| | −2 | 0 | 2 | 4 | 6 | 8 |
| Percent change in the ratio of $I_{Ca,L}$ $\tau$ to QT or APD | >+10% | +10% to −10% | <−10% to −15% | <−15% to −25% | <−25% to −35% | <−35% |

*The maximal TdP score is 12; the minimal TdP score is −3.

In addition to providing novel methods for screening a test compound for its risk of inducing TdP, the present invention provides methods for screening a test compound for its antiarrhythmic therapeutic potential and efficacy. The proarrhythmic potential of a compound is reversely proportional to the ratio of the recovery time constant ($\tau$) of $I_{Ca,L}$ to ventricular repolarization time. In other words, a smaller ratio corresponds to a higher risk that the compound induces TdP. In contrast, the antiarrhythmic potential of a compound is directly proportional to repolarization time and the ratio of the recovery time constant ($\tau$) of $I_{Ca,L}$ to ventricular repolarization time. That is, a greater ratio plus a longer repolarization time corresponds to a higher antiarrhythmic potential of the compound. This is because the development of arrhythmias via the reentrant mechanism is determined by the wavelength of the reentrant impulse and the size of the circuit. The wavelength of the reentrant impulse should be significantly less than the length of the reentrant circuit so that a fully excitable gap is present between the crest and the tail of the reentrant wavefront for the maintenance of circus movement. The wavelength of the reentrant impulse is equal to the conduction velocity times the effective refractory period of myocardial muscle in the pathway that is influenced by repolarization time and recovery of inward currents (Kowey and Yan, Heart Rhythm 2005; in press). The present invention is, therefore, useful not only in screening test compounds for their capacity to cause TdP, but also in screening test compounds for their efficacy in the inhibition of cardiac arrhythmias such as atrial fibrillation and monomorphic ventricular tachycardia The following examples are provided to illustrate the invention in greater detail. The examples are intended to illustrate, not to limit, the invention.

EXAMPLE 1

Figure 2A:
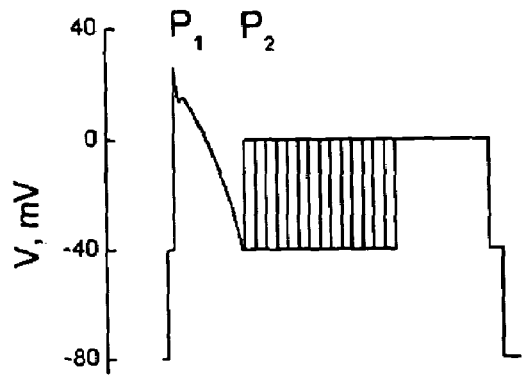
FIG. 2. Recovery Kinetics of L-type Calcium Channel Current. (a). Graphical depiction of the voltage clamping protocol used for the assessment of $I_{Ca,L}$ recovery from inactivation in single ventricular myocytes. (b). Graphical depiction of original tracings of $I_{Ca,L}$ recordings. (c). Time course of $I_{Ca,L}$ recovery from inactivation in mouse, rabbit, guinea pig, dog, and cow.
Figure 2B:
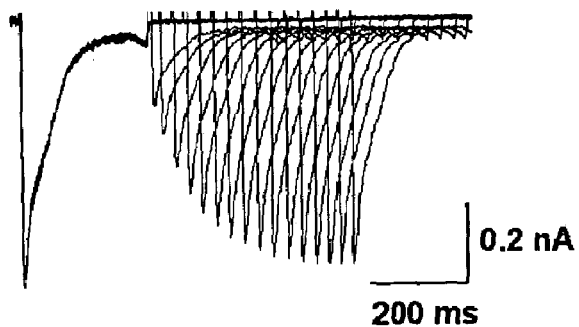
Figure 2C:
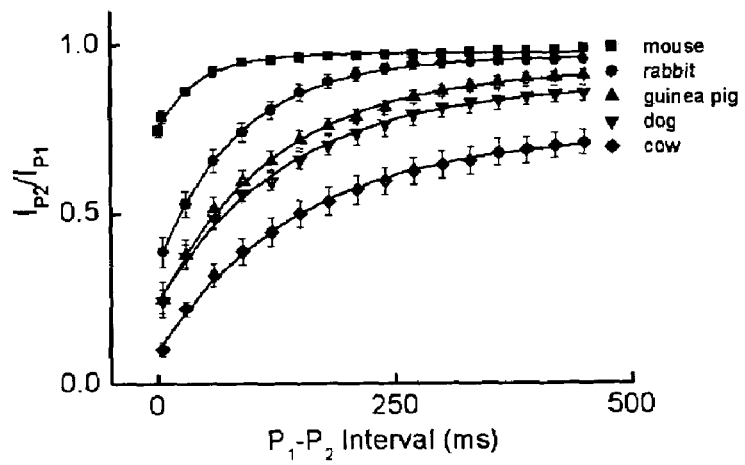
Figure 3A:
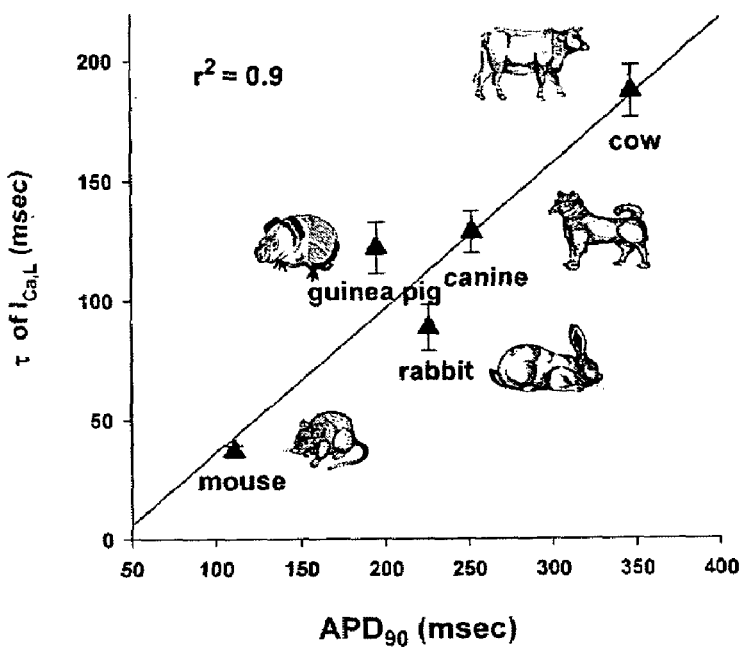
FIG. 3. Action Potential Repolarization and $I_{Ca,L}$ Recovery (a) Comparison of the recovery time constant ($\tau$) of $I_{Ca,L}$ for mouse, guinea pig, rabbit, canine and cow left ventricles is shown. (b). Comparison of the ratio of the $\tau$ of $I_{Ca,L}$ recovery to subendocardial or endocardial action potential duration for mouse, guinea pig, rabbit, canine and cow left ventricles is shown. (c). Graphical depiction of original recordings of transmembrane action potentials and ECG in control and the presence of dofetilide in an isolated rabbit left ventricular wedge preparation. (d). Graphical depiction of original recordings of transmembrane action potentials and ECG in control and the presence of dofetilide plus azimilide in an isolated guinea pig left ventricular wedge preparation. $APD_{90}$: action potential duration at 90% repolarization; EAD: early after depolarization.
Figure 3B:
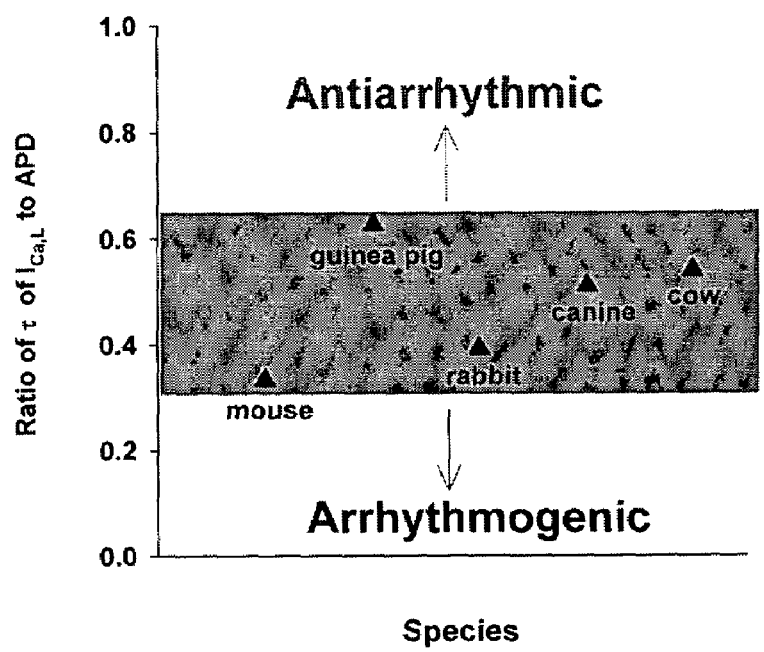

Comparison of Recovery Time Constant ($\tau$) of $I_{Ca,L}$ in Representative Mammals In preliminary experiments, the time course of L-type calcium current ($I_{Ca,L}$) recovery from inactivation in mice, guinea pigs, rabbits, dogs and cows was examined. As shown in FIG. 2, the recovery kinetics of $I_{Ca,L}$ at −40 mV were different among these species, and there was a linear relationship between the time constant ($\tau$) of $I_{Ca,L}$ recovery and the corresponding ventricular repolarization time ($r^2$=0.90, p<0.05; FIG. 3a). The data show that although the left ventricular repolarization time was markedly different among these species (FIG. 1), the ratio of $\tau$ of $I_{Ca,L}$ recovery to the longest ventricular repolarization time remained fairly consistent among them (FIG. 3b). This indicated that an adequate and constant ratio of the time constant $\tau$ of $I_{Ca,L}$ recovery to ventricular APD serves as a stabilizer of cardiac cell membrane potential during repolarization phase 2.

Figure 3C:
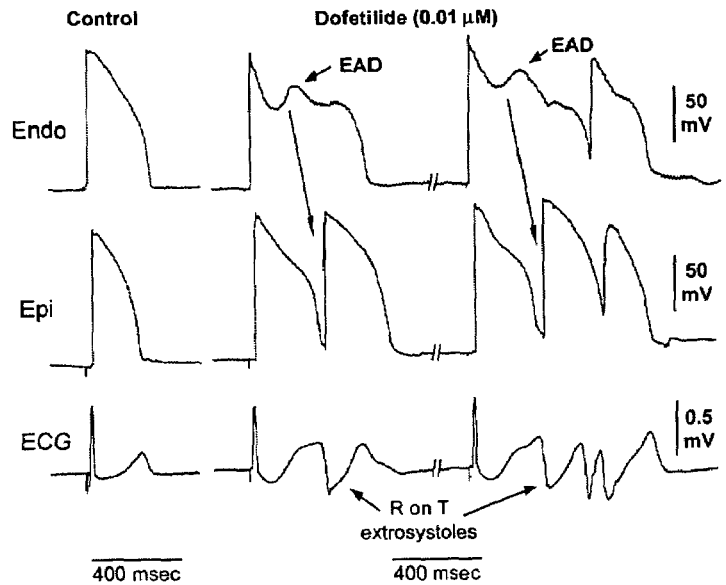
Figure 3D:
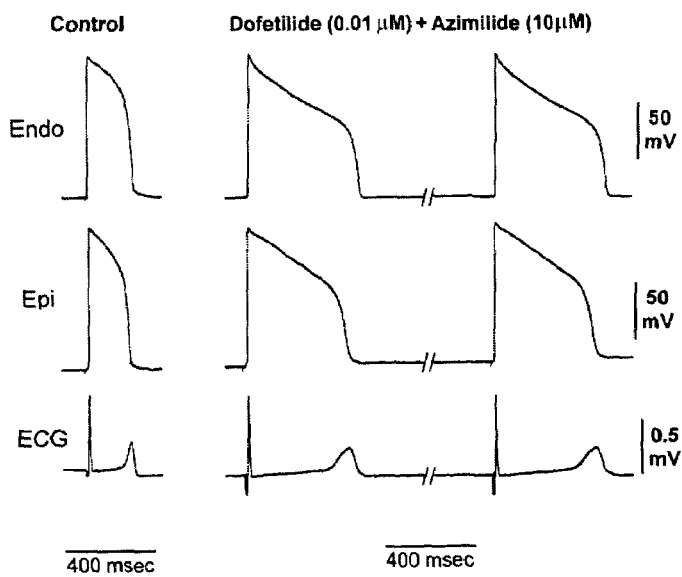

Without intending to be limited to any particular theory or mechanism of action, it is believed that if the intrinsic ratio of the $\tau$ of $I_{Ca,L}$ recovery to the ventricular repolarization time serves as a stabilizer for the cellular membrane, an increase in this ratio would be antiarrhythmic, inhibiting the genesis of EAD. In contrast, a reduction of this ratio would be arrhythmogenic, leading to action potential instability during ventricular repolarization (FIG. 3b). Mice and rabbits were found to have relatively smaller intrinsic ratios among species investigated (FIG. 3b), while guinea pigs possessed the greatest. This indicates that the mouse and rabbit hearts may have a higher potential to develop EADs due to such hearts' relatively faster $I_{Ca,L}$ recovery during repolarization. In fact, EADs and TdP are readily induced in the rabbit heart preparations under pathophysiological conditions or pharmacological intervention (Yan et al., *Circulation* 2001; 103: 2851-2856; Yan et al., *Am. J. Physiol.* 2001 281: H1968-H1975). In contrast, the guinea pig hearts, which were determined to have a greater ratio of the $\tau$ of $I_{Ca,L}$ recovery to ventricular repolarization time, rarely develop spontaneous TdP under similar conditions (Gerhardy et al., *Basic Res. Cardiol.* 1998; 93: 285-294). A further test of this notion is shown in FIGS. 3c and 3d. Dofetilide at 0.003 µM, a concentration close to its $IC_{50}$ to block the rapidly activating delayed rectifier potassium current ($I_{Kr}$), markedly increased rabbit endocardial $APD_{90}$ from 252±8 to 443±27 ms (76%, n=8, p<0.01), leading to the development of EAD in seven of eight rabbit left ventricular wedge preparations. A further increase in dofetilide dose (0.01 µM) resulted in TdP in all of eight rabbits (FIG. 3c). On the other hand, a combination of dofetilide (0.01 µM) and azimilide (10 µM) resulted in a comparable increase in Guinea pig endocardial $APD_{90}$ (126%, from 195±2 to 440±33 ms, n=5, p<0.01) without inducing EAD in any of the five experiments (p<0.01 compared with the rabbit).

EXAMPLE 2

Rabbit Left Ventricular Wedge Preparation and Electrophysiological Recordings

Rabbit Ventricular Wedge Preparation:

Female rabbits weighting 2.5-3 kg were anticoagulated with heparin and anesthetized with pentobarbital (30-35 mg/kg, i.v.). The chest was opened via a left thoracotomy, and the heart was excised and placed in a cardioplegic solution consisting of cold (4° C.) normal Tyrode's solution. Transmural wedges with dimensions of approximately 1.5 cm wide and 2-3 cm long were dissected from the left ventricle. The wedge tissue was cannulated via the circumflex or left main artery and perfused with cardioplegic solution. The preparation was then placed in a small tissue bath and arterially perfused with Tyrode's solution containing 4 mM $K^+$ buffered with 95% $O_2$ and 5% $CO_2$ (T: 35.7±0.1° C., perfusion pressure: 35-45 mmHg). The ventricular wedge was allowed to equilibrate in the tissue bath until electrically stable, approximately one hour. The preparations were stimulated at basic cycle lengths (BCL) of 1000 and 2000 ms using bipolar silver silver electrodes insulated except at the tips and applied to the endocardial surface.

ECG and Transmembrane Action Potential Recordings:

A transmural ECG signal was recorded in all experiments using extracellular silver/silver chloride electrodes placed in the Tyrode's solution bathing the preparation. Electrodes were placed 1.0 to 1.5 cm from the epicardial and endocardial surfaces, along the same vector as the transmembrane recordings (Epi: "+" pole). The QT interval was defined as the time from the onset of the QRS to the point at which the final downslope of the T wave crosses the isoelectric line. Transmembrane action potentials were recorded simultaneously from epicardial and endocardial sites of the rabbit left ventricular wedge preparations. The action potential duration was measured at 90% repolarization ($APD_{90}$).

EXAMPLE 3

Screening of Compounds in Ventricular Wedge Preparations

The following compounds were evaluated for their dose-dependent effect on the QT interval in the ventricular wedge preparations: quinidine, sotalol, bepridil, haloperidol, moxifloxacin, flecainide, citalopram, loratadine, fluxetine and verapamil. Each of these ten compounds was tested in 4 doses ranging from their free therapeutic plasma $C_{max}$ to the concentration closely to or greater than 30-fold over the $C_{max}$. After the wedge preparations were perfused with normal Tyrode's solution for one hour in the chamber, control transmembrane action potentials and a transmural ECG were recorded. The preparations were then switched to Tyrode's solution containing a test compound with each dose for 20 minutes.

EXAMPLE 4

Preparation of Single Rabbit Ventricular Myocytes and Electrophysiological Recordings Single rabbit ventricular myocytes were isolated using the enzymatic digestion method as described in Rials et al., *Circulation* 1997; 96:1330-1336. The rabbit heart was initially perfused with 500 ml $Ca^{2+}$-free solution (in mM: NaCl 125, KCl 3.5, $KH_2PO_4$ 1.5, $MgCl_2$ 1, $NaHCO_3$ 20, glucose 10) gassed with 95% $O_2$-5% $CO_2$ at 37° C. at a rate of 30 ml/min with a peristaltic pump. The heart was then perfused with 80 ml enzyme solution (48 mg collagenase (type II), 12 mg hyaluronidase, 80 mg BSA, and 300 mg taurine to the $Ca^{2+}$-free solution). The enzyme solution passed through the heart a single time before 40 ml, and recirculation after 40 ml. Ten minutes later, 7 mg protease XIV was added to the enzyme solution, and the heart was perfused for an additional 10 minutes. At the end of enzyme perfusion, a thin layer (<1.5 mm) of tissue was dissected from endocardial surface of the middle ⅔ of left ventricular free wall (excluding apex and base). Myocytes were dispersed in recovery medium (in mM: potassium glutamate 80, $K_2HPO_4$ 20, KCl 20, $MgCl_2$ 5, $K_2EGTA$ 0.5, $Na_2ATP$ 2, Na-pyruvate 5, creatine 5, taurine 20, glycine 10, glucose 10, and HEPES 5, DNase I 0.05 mg/ml). Twenty minutes after dispersion, cells was transferred to Tyrode's solution (in mM: NaCl 137, KCl 5, $MgCl_2$ 1, $CaCl_2$ 1, glucose 10, HEPES 10; pH=7.4) and stored at 10° C.

$I_{Ca,L}$ was recorded in rabbit single ventricular myocytes at 35.7±0.1° C. using the whole-cell voltage-clamp technique as described by Linz and Meyer, *Pflugers Arch.* 2000; 439:588-599. The time course of $I_{Ca,L}$ recovery was examined using a double-pulse protocol. Since the recovery of $I_{Ca,L}$ from inactivation is not only time dependent but also voltage dependent, action potential configuration during phase 1 and 2 may influence $I_{Ca,L}$ recovery.

The action potentials were first recorded from the endocardium of the rabbit left ventricular wedge preparation at a basic cycle length of 2000 ms before and after exposure to a test compound. The action potential tracing ($P_1$) and subsequent squire pulses ($P_2$) were then used for voltage clamp from holding potential of −40 mV. The interpulse intervals for the voltage clamp ranged from 5 ms to 600 ms. The peak current ratios of $I_{P2}$ to $I_{P1}$ were plotted on the ordinate as a function of the interpulse interval. The data were fitted with single exponential ($y=y_0+Ae^{-(x-x0)/\tau}$) to obtain $I_{Ca,L}$ recovery time constant ($\tau$).

EXAMPLE 5

Calculation of the Ratio of $I_{Ca,L}$ Recovery Time Constant to Endocardial $APD_{90}$ and the TdP Risk Score The ratio of $I_{Ca,L}$ recovery time constant to endocardial $APD_{90}$ under control and after exposure to one of the test compounds described above was determined as follows: the ratio equals $\tau(ms)/APD_{90}$ (ms). The relative TdP risk score was then calculated based on the change in the QT interval and the ratio according to the criteria listed in Table 1. Antiarrhythmic potential of a test compound is proportional not only to its effect to prolong cardiac repolarization but also on the ratio of $I_{Ca,L}$ recovery time constant to repolarization. This is because the prolongation of repolarization and an increase in the ratio of $I_{Ca,L}$ recovery time constant to repolarization is associated with an increase in the effective refractory period of action potential that inhibits cardiac arrhythmias via the mechanism of reentry such as atrial fibrillation and monomorphic ventricular tachycardia.

Statistical analyses were carried out using a Student's t test for paired data or One Way ANOVA coupled with Schefe's test. The $X^2$ test was used for comparisons between 2 groups for event incidences. All results were expressed as means ±SEM unless otherwise indicated.

Figure 4:
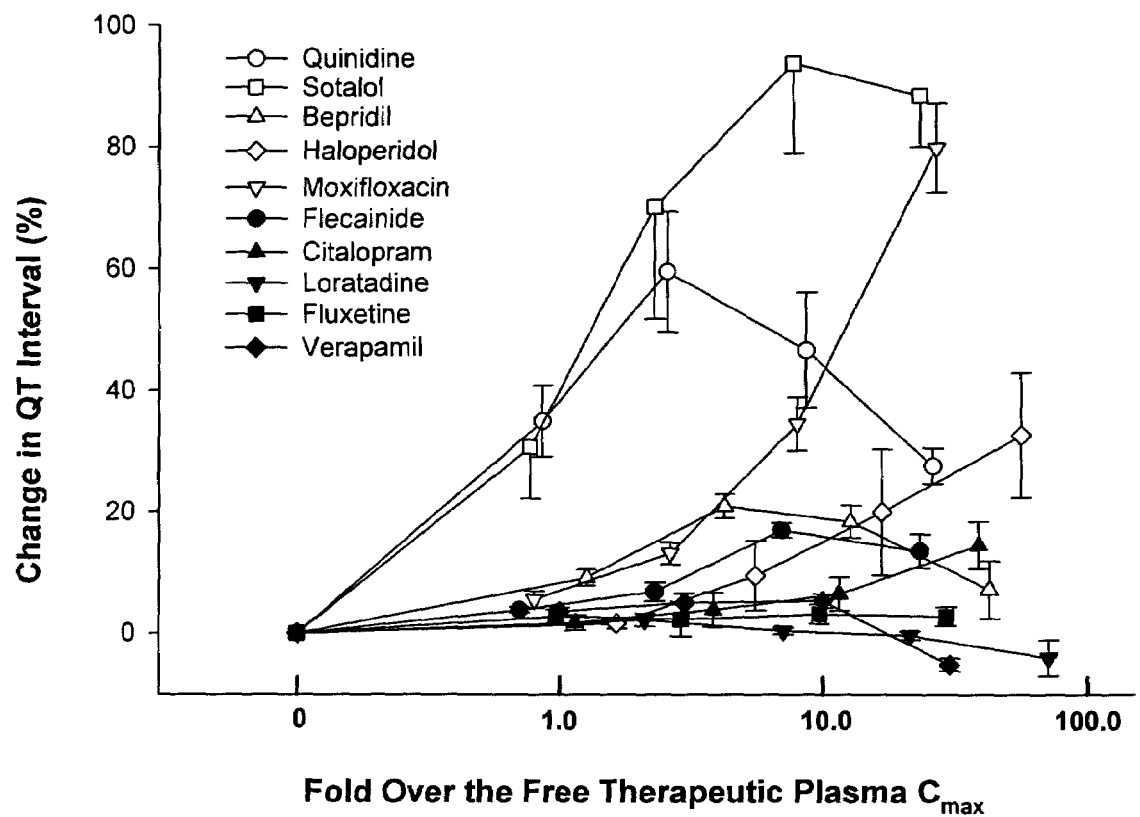
FIG. 4. Comparison of Dose-dependent Effect on QT Intervals. The dose-dependent effect on the QT interval among quinidine, sotalol, bepridil, haloperidol, moxifloxacin, flecainide, citalopram, loratadine, fluxetine and verapamil in rabbit heart preparations was compared. Isolated rabbit left ventricular wedge preparations were treated with the compounds in a concentration equivalent to the free therapeutic plasma Cmax up to concentrations 100-fold over the Cmax. A transmural ECG was concurrently recorded. The results shown in FIG. 4 demonstrate the effect of the concentration of the drug on QT interval. n=5 preparations for each compound.

The dose-dependent effect on the QT interval among quinidine, sotalol, bepridil, haloperidol, moxifloxacin, flecainide, citalopram, loratadine, fluxetine and verapamil in rabbit heart preparations was compared. Isolated rabbit left ventricular wedge preparations were treated with the compounds in a concentration equivalent to the free therapeutic plasma Cmax up to concentrations 100-fold over the Cmax. A transmural ECG was concurrently recorded. The results shown in FIG. 4 demonstrate the effect of the concentration of the drug on the QT interval. n=5 preparations for each compound.

Figures 5A, 5B:
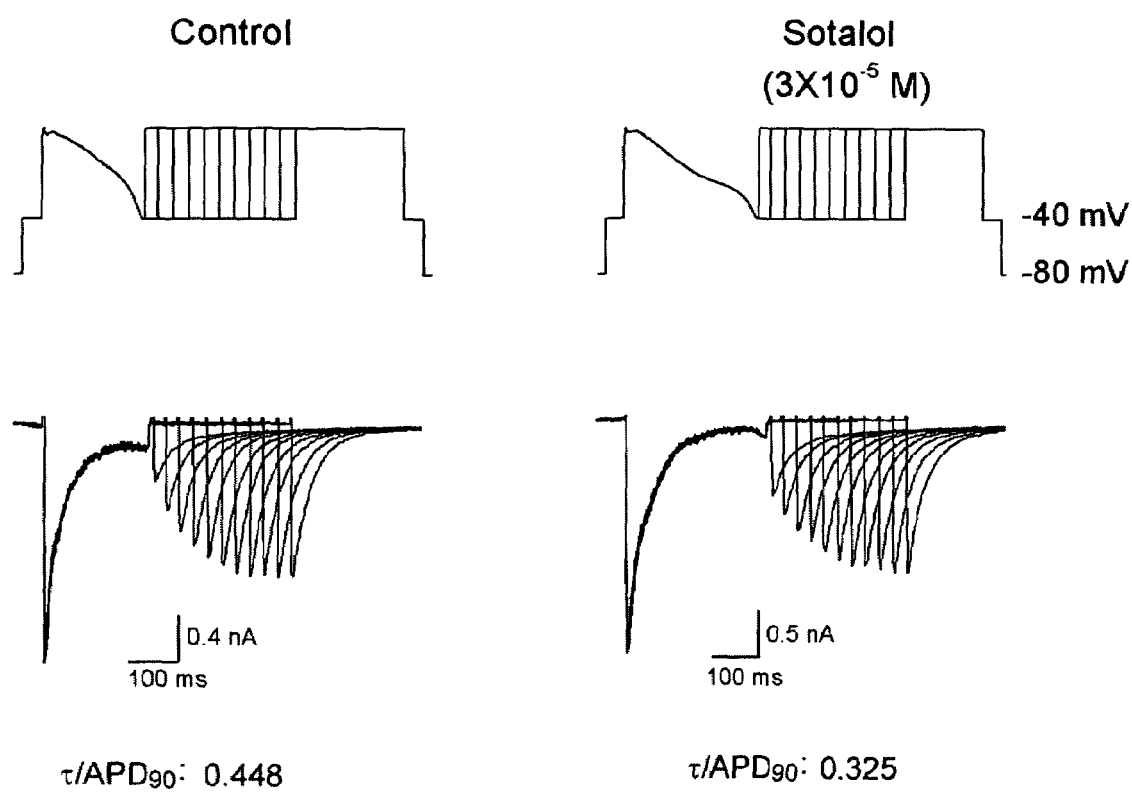
FIG. 5. Example of $I_{Ca,L}$ Recording Before and After Exposure to Test Compound. (a). Original recordings of $I_{Ca,L}$ in the absence of Sotalol. (b). Original recordings of $I_{Ca,L}$ in the presence of Sotalol. The ratio of the $I_{Ca,L}$ recovery time constant ($\tau$) to endocardial APD at 90% repolarization ($APD_{90}$) was 0.448 in control and 0.325 in the presence of Sotalol at 30 µM.

The L-type calcium channel current ($I_{Ca,L}$) was measured both before and after exposure to quinidine, sotalol, bepridil, haloperidol, moxifloxacin, flecainide and citalopram. and compared to exposure with control compounds such as loratadine, fluxetine and verapamil. An exemplary example of these measurements, carried out for sotalol, is shown in FIG. 5. In this specific example, sotalol, a QT prolonging drug with a high TdP risk in humans, reduced the ratio of $I_{Ca,L}$ recovery time constant to endocardial $APD_{90}$ from the control of 0.448 to 0.325 at dose of 30 μM, a concentration only 2.9-fold higher this drug's free therapeutic plasma $C_{max}$ for humans.

Figure 6:
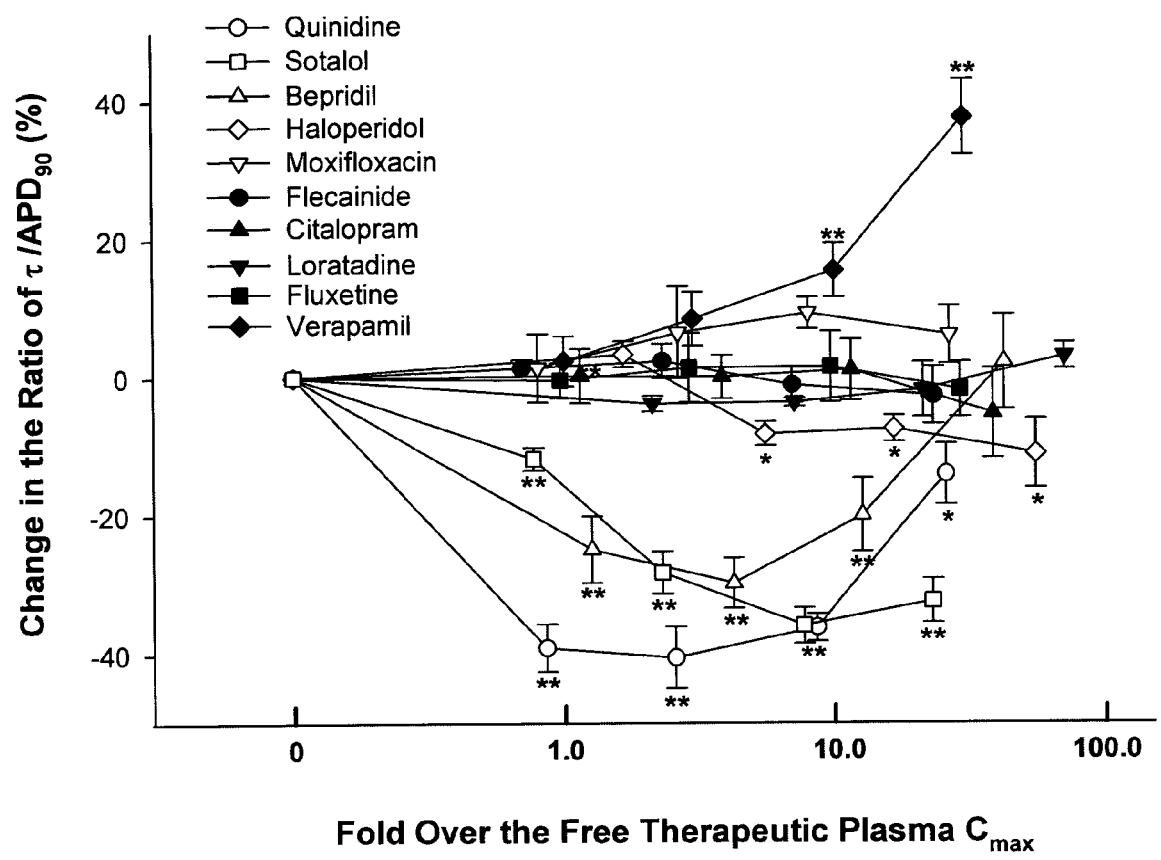
FIG. 6. Graphical Comparison of the Percent-Change in $I_{Ca,L}$ Recovery Time Constant (τ) to Endocardial $APD_{90}$. The drug-induced percent change in the ratio of $I_{Ca,L}$ recovery time constant to endocardial $APD_{90}$ was calculated for quinidine, sotalol, bepridil, haloperidol, moxifloxacin, flecainide, citalopram, loratadine, fluxetine and verapamil. The percent change is shown. n=5 for each compound. * and ** indicate p<0.05 and p<0.01, respectively, when compared with that in the absence of drug.

The drug-induced percent change in the ratio of $I_{Ca,L}$ recovery time constant to endocardial $APD_{90}$ was calculated for quinidine, sotalol, bepridil, haloperidol, moxifloxacin, flecainide, citalopram, loratadine, fluxetine and verapamil. The percent change is shown in FIG. 6. n=5 for each compound. * and ** indicate p<0.05 and p<0.01, respectively, when compared with that in the absence of drug.

Figure 7:
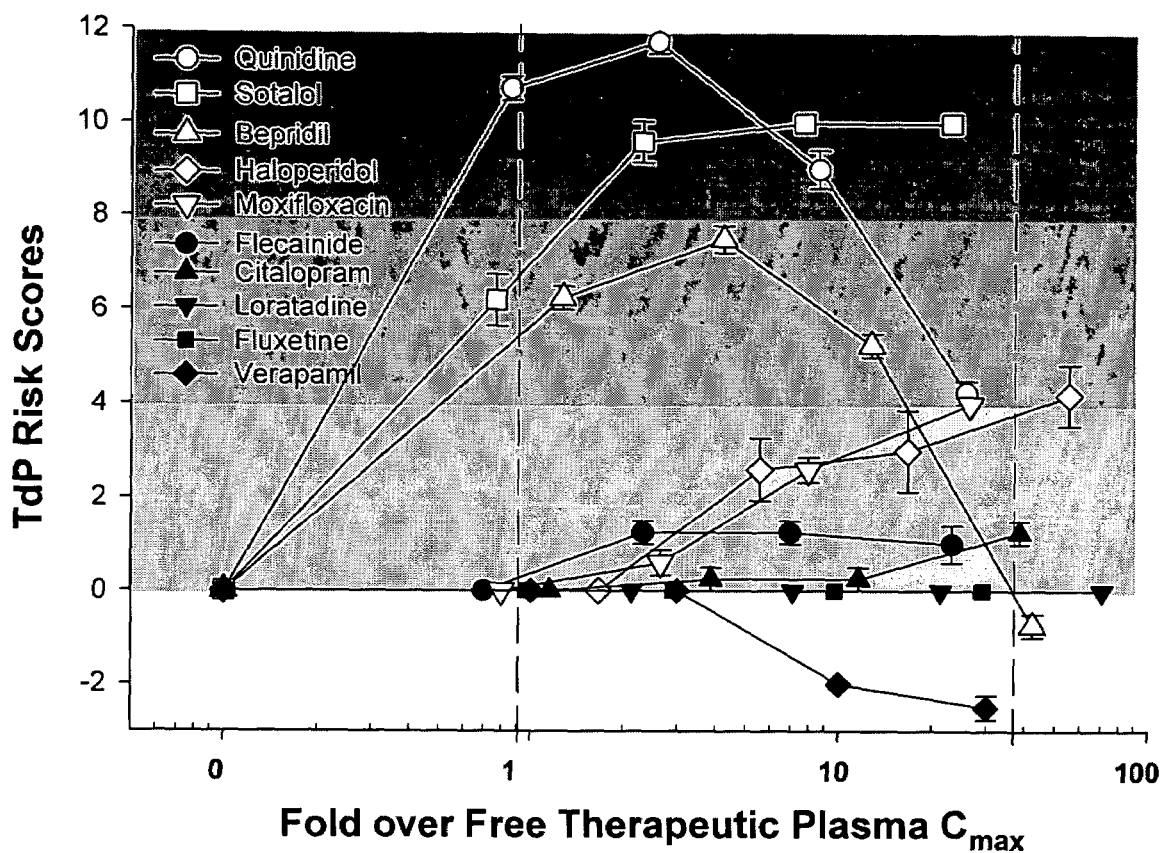
FIG. 7. TdP Score. Using on the criteria in Table 1, below, the TdP scores of test compounds were calculated, and the calculated scores at each dose are shown. The relative TdP are compared among quinidine, sotalol, bepridil, haloperidol, moxifloxacin, flecainide, citalopram, loratadine, fluxetine and verapamil. The maximal TdP score in the testing concentration range is ranked from high to low: quinidine (11.75±0.22), sotalol (10.00±0.00), bepridil (7.50±0.26), haloperidol (4.20±0.58), moxifloxacin (4.00±0.00), flecainide (1.25±0.22), citalopram (1.25±0.22), fluxetine (0.00±0.00), loratadine (−0.25±0.22) and verapamil (−2.50±0.26). Relative risk is indicated by background shading: white/no shading corresponds to a negative risk of inducing TdP, light gray corresponds to a low risk, halftone gray corresponds to a moderate risk, and dark gray corresponds to a high risk.

Using the criteria in Table 1, the TdP scores of test compounds were calculated, and the calculated scores at each dose are shown in FIG. 7. The relative TdP are compared among quinidine, sotalol, bepridil, haloperidol, moxifloxacin, flecainide, citalopram, loratadine, fluxetine and verapamil. The maximal TdP score in the testing concentration range is ranked from high to low: quinidine (11.75±0.22), sotalol (10.00±0.00), bepridil (7.50±0.26), haloperidol (4.20±0.58), moxifloxacin (4.00±0.00), flecainide (1.25±0.22), citalopram (1.25±0.22), fluxetine (0.00±0.00), loratadine (−0.25±0.22) and verapamil (−2.50±0.26). These drugs were ranked according to their relative risk of inducing TdP, as shown in Table 2. The relative risk was categorized as negative, low, moderate, and high risk.

TABLE 2

Relative ranking of TdP Risk for compounds tested using the inventive methods.

| TdP Risk Category | Drug Name | Maximal TdP Score |
|---|---|---|
| Negative TdP Risk | verapamil | −2.5 ± 0.3 |
|  | loratadine | −0.3 ± 0.2 |
|  | fluxetine | 0.0 ± 0.0 |
| Low TdP Risk | citalopram | 1.3 ± 0.2 |
|  | flecainide | 1.3 ± 0.2 |
|  | moxifloxacin | 4.0 ± 0.0 |
| Moderate TdP Risk | haloperidol | 4.2 ± 0.6 |
|  | bepridil | 7.5 ± 0.3 |
| High TdP Risk | sotalol | 10.0 ± 0.0 |
|  | quinidine | 11.8 ± 0.2 |

What is claimed is:

1. A method for screening compounds for their potential to induce or inhibit a cardiac arrhythmia in a subject, comprising determining the ratio of the time constant ($\tau$) of $I_{Ca,L}$ recovery in tissue expressing the L-type calcium channel or any subunit or combination thereof of the L-type calcium channel treated with a test compound to the ventricular repolarization time of cardiac tissue treated with the test compound.

2. The method of claim 1, wherein determining the ratio comprises measuring the ventricular repolarization time of cardiac tissue treated with the test compound, measuring the recovery of the L-type calcium channel current ($I_{Ca,L}$) in tissue expressing the L-type calcium channel or any subunit or combination thereof of the L-type calcium channel treated with the test compound, calculating the time constant of ($\tau$) of $I_{Ca,L}$ recovery in the tissue expressing the L-type calcium channel or any subunit or combination of subunits of the L-type calcium channel, and calculating the ratio of the time constant ($\tau$) of $I_{Ca,L}$ recovery to the ventricular repolarization time.

3. The method of claim 2, wherein the ventricular repolarization time is measured by electrogram, glass microelectrode, or monophasic action potential electrode and concurrent transmural electrocardiogram.

4. The method of claim 2, wherein the cardiac tissue is freshly isolated ventricular myocytes, freshly isolated Purkinje fibers, freshly isolated ventricular myocardial layer, freshly isolated papillary muscle, freshly isolated atrial tissue, freshly isolated ventricular wedge, or freshly isolated atrial wedge.

5. The method of claim 2 wherein the L-type calcium channel current recovery is measured by voltage clamping.

6. The method of claim 1, wherein the tissue expressing the L-type calcium channel or any subunit or combination thereof of the L-type calcium is cardiac tissue.

7. The method of claim 1, wherein the tissue expressing the L-type calcium channel or any subunit or combination thereof of the L-type calcium is a stable cell line.

8. The method of claim 6, wherein the cardiac tissue is freshly isolated ventricular myocytes, freshly isolated Purkinje fibers, freshly isolated ventricular myocardial layer, freshly isolated papillary muscle, freshly isolated atrial tissue, freshly isolated ventricular wedge, or freshly isolated atrial wedge.

9. The method of claim 2, wherein the tissue expressing the L-type calcium channel or any subunit or combination thereof of the L-type calcium is cardiac tissue.

10. The method of claim 2, wherein the tissue expressing the L-type calcium channel or any subunit or combination thereof of the L-type calcium is a stable cell line.

11. The method of claim 9, wherein the cardiac tissue is freshly isolated ventricular myocytes, freshly isolated Purkinje fibers, freshly isolated ventricular myocardial layer, freshly isolated papillary muscle, freshly isolated atrial tissue, freshly isolated ventricular wedge, or freshly isolated atrial wedge.

12. The method of claim 1, wherein the cardiac tissue and tissue expressing the L-type calcium channel or any subunit or combination thereof of the L-type calcium channel are treated with multiple doses of the test compound wherein the doses range from the rest compound's free therapeutic plasma $C_{max}$ to a concentration equal to or greater than 100-times higher than the free therapeutic plasma $C_{max}$.

13. The method of claim 1, wherein the cardiac tissue and tissue expressing the L-type calcium channel or any subunit or combination thereof of the L-type calcium channel are treated with multiple doses of the test compound wherein the doses range from the test compound's free therapeutic plasma $C_{max}$ to a concentration equal to or greater than 30-time higher than the free therapeutic plasma $C_{max}$.

14. The method of claim 2, wherein the cardiac tissue and tissue expressing the L-type calcium channel or any subunit or combination thereof of the L-type calcium channel are treated with multiple doses of the test compound wherein the doses range from the test compound's free therapeutic plasma $C_{max}$ to a concentration equal to or greater than 100-times higher than the free therapeutic plasma $C_{max}$.

15. The method of claim 2, wherein the cardiac tissue and tissue expressing the L-type calcium channel or any subunit or combination thereof of the L-type calcium channel are treated with multiple doses of the test compound wherein the doses range from the test compound's free therapeutic plasma $C_{max}$ to a concentration equal to or greater than 30-times higher than the free therapeutic plasma $C_{max}$.

16. The method of claim 1, further comprising determining a TdP risk score for a specified dose of the test compound in a specified species by comparing said ratio of said time constant ($\tau$) of $I_{Ca,L}$ recovery to said ventricular repolarization time for said test compound to the ratio of said time constant ($\tau$) of $I_{Ca,L}$ recovery to said ventricular repolarization time of a standard having an established negative, low, moderate, or high risk of inducing TdP in said species.

17. The method of claim 16, wherein the standard having an established negative risk of inducing TdP is LORATADINE, CIPROFLOXACIN, CLOMIPRAMINE, FLUXETINE or VERAPAMIL.

18. The method of claim 16, wherein the standard having an established low risk of inducing TdP is AMIODARONE, CITALOPRAM, FLECAINIDE, or MOXIFLOXACIN.

19. The method of claim 16, wherein the standard having an established moderate risk of inducing TdP is BEPRIDIL, HALOPERIDOL, SPARFLOXACIN, or TERFENADINE.

20. The method of claim 16, wherein the standard having an established high risk of inducing TdP is DOFETILIDE, SOTALOL, QUINIDINE, or CISAPRIDE.

* * * * *

UNITED STATES PATENT AND TRADEMARK OFFICE
CERTIFICATE OF CORRECTION

PATENT NO. : 7,396,524 B2
APPLICATION NO. : 11/194983
DATED : July 8, 2008
INVENTOR(S) : Gan Xin Yan It is certified that error appears in the above-identified patent and that said Letters Patent is hereby corrected as shown below:

Column 18, line 2, delete "30-time" and insert therefor --30-times--.

Signed and Sealed this

Fourth Day of November, 2008

JON W. DUDAS
*Director of the United States Patent and Trademark Office*